United States Patent [19]

Balakrishnan

[11] Patent Number: 4,965,736
[45] Date of Patent: Oct. 23, 1990

[54] CROSS-DIRECTIONAL CONTROL OF SHEETMAKING SYSTEMS

[75] Inventor: Ramesh Balakrishnan, Stanford, Calif.

[73] Assignee: Measurex Corporation, Cupertino, Calif.

[21] Appl. No.: 207,412

[22] Filed: Jun. 15, 1988

[51] Int. Cl.⁵ .............................................. G06F 15/46
[52] U.S. Cl. ...................... 364/469; 162/253; 162/263; 364/152; 364/471; 364/554; 364/572
[58] Field of Search .............. 364/469, 552, 554, 568, 364/575, 576, 572, 471, 724.12, 724.18, 728.01, 725, 726, 148, 152, 571.01; 162/252, 253, 258, 262, 263, DIG. 6, DIG. 10

[56] References Cited

U.S. PATENT DOCUMENTS

| | | |
|---|---|---|
| 3,496,344 | 2/1970 | Chope .................... 162/DIG. 10 X |
| 3,557,351 | 1/1971 | Doering .............................. 364/572 |
| 4,453,404 | 6/1984 | Powell ...................... 162/DIG. 6 X |
| 4,648,712 | 3/1987 | Brenholdt ........................ 162/263 X |
| 4,674,045 | 6/1987 | Kerber et al. ................... 364/726 X |
| 4,707,779 | 11/1987 | Hu .................................... 364/471 X |

Primary Examiner—Joseph Ruggiero
Attorney, Agent, or Firm—Burns, Doane, Swecker & Mathis

[57] ABSTRACT

A system and method for controlling sheetproducing machines includes measurement devices for measuring properties of a sheet at cross-directional locations to provide cross-directional profiles, and spatial-frequency splitting means for separating low spatial-frequency components from high spatial-frequency components for each profile. The separated high and low spatial-frequency components provide operating signals to controllably adjust properties of the sheet.

24 Claims, 8 Drawing Sheets

CROSS-DIRECTIONAL CONTROL OF SHEETMAKING SYSTEMS

BACKGROUND OF THE INVENTION

1. Field of the Invention

The present invention generally relates to systems for controlling sheetmaking machines and, more particularly, to control systems that employ measuring devices that obtain cross-directional profiles across sheets during production.

2. State of the Art

It is common practice to make on-line measurements of sheet properties during sheet processing. The purpose of on-line measurements is to enable prompt control of sheet processing and, thus, to increase sheet uniformity and to reduce the quantity of substandard sheet material that is produced before undesirable process conditions are corrected. In papermaking, for instance, on-line sensors detect properties such as basis weight, moisture content, and caliper of paper sheets.

It is well known that on-line measurements can be made by sensors that periodically traverse, or "scan", traveling sheets in the cross direction, i.e., in a direction extending across the sheet surface generally perpendicular to the direction of sheet travel. In practice, scanning sensors typically travel at a rate of about ten inches per second and provide an integrated output about every fifty milliseconds; thus, a typical scanning sensor provides about one measurement output per each half-inch in the cross direction. Measurement information detected by scanning sensors is often assembled to provide graph-like "profiles" composed of successions of measurements at adjacent locations in the cross direction, which locations are usually are referred to as "slices". Equivalent cross-directional profiles also can be obtained by measurement systems that employ arrays of fixed sensors that extend in the cross direction.

To control sheetprocessing machines to produce uniform quality sheets, it is common practice to detect variations that occur both between and within cross-directional profiles. In the machine direction, sheet uniformity can be defined as a measured sheet property being constant from profile to profile along any given slice. In the cross direction, sheet uniformity can be defined as a measured sheet property being constant from slice to slice; thus, cross-directional sheet uniformity implies flat profiles.

Various devices are known to control sheet properties in the cross direction and, hence, to control cross-directional profiles. In papermaking, for instance, basis weight can be controlled in the cross direction by a headbox, either of the primary or secondary type. As another example, variations in moisture across a paper sheet can be controlled by a re-moisturizing shower which has independently controllable segments in the cross direction.

A difficulty in using profile measurements for cross-directional control of sheet properties arises when a sheetprocessing machine employs two or more profiling devices that are both capable of affecting the same property of a sheet. During the manufacture of paper, for instance, sheet moisture can be adjusted in the cross direction by both steamboxes and remoisturizing showers and, often, papermaking machines include both devices. As another example from the papermaking field, basis weight can be adjusted in the cross direction by both primary and secondary headboxes, and some papermaking machines include both devices. In such situations, a question arises as to how the two devices should be controlled when the control signals for both devices, at any given time, are derived from the same cross-directional profile.

In conventional control practice, multiple control devices on sheetprocessing machines are often operated with actuating signals distributed, at any given time, according to a predetermined ratio. As one example, where both a re-moisturizing shower and a steambox are employed on the same papermaking machine, a conventional control strategy might be that, for a given magnitude of the actuating signal at a given time, the re-moisturizing shower is turned on one-fourth and the steam box is turned on one-eighth. Then, according to this example, when the actuating signal doubles in magnitude, the remoisturizing shower is turned on one-half and the steam box one-quarter. Such practice is often referred to as "ratioing" of signals.

Another conventional strategy for operating two or more control devices on a sheetprocessing machine is called "mid-ranging". In a typical mid-ranging strategy, a first control device is operated as long as the set points of its actuators fall within predetermined limits, i.e., within a defined "mid-range". Then, when one or more of the set points moves outside the mid-range, a second control device is actuated. Normally, limits for the mid-ranges are selected based upon prior operating experience and by the capabilities of the control device actuators It should be appreciated that conventional control strategies, such as ratioing and mid-ranging techniques, do not necessarily result in optimum results when applied to control devices on sheetprocessing machines. In other words, conventional control strategies do not necessarily achieve optimum use of the control device which is best suited to adjust process conditions to overcome detected non-uniformities in sheet profiles.

DETAILED DESCRIPTION OF THE PREFERRED EMBODIMENT

Figure 1:
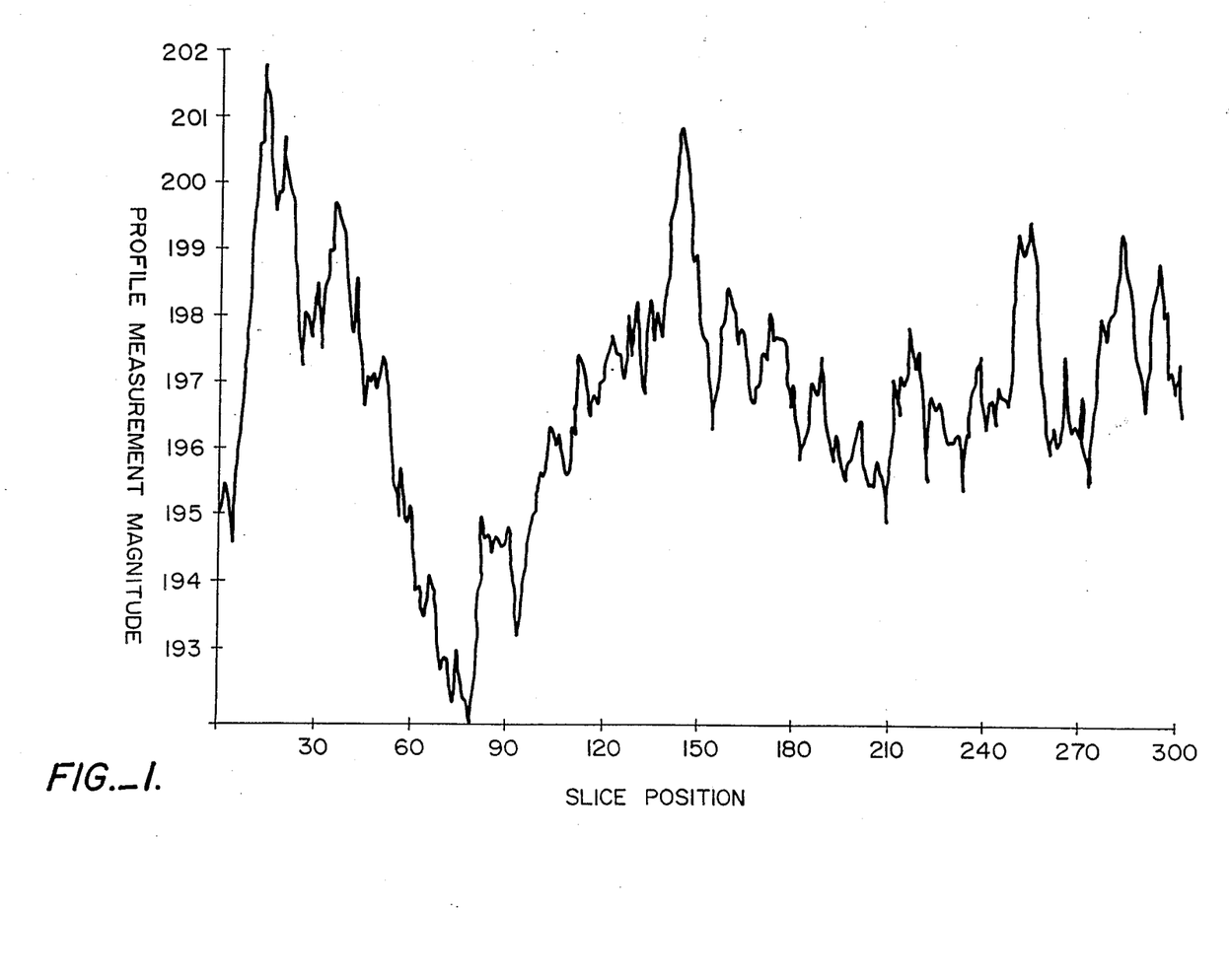
FIG. 1 is a graph depicting a typical profile comprised of successive measurements taken in the cross direction of a travelling sheet.

FIG. 1 shows an example of a cross-directional profile provided by a measurement system which has measured a selected property of a sheet at successive cross-directional locations. In FIG. 1, values along the vertical axis indicate the magnitude of the measured property; those values could represent, for example, a sheet property such as basis weight, moisture content or caliper. Values on the horizontal axis in FIG. 1 indicate the cross-directional location, or slice, at which the selected property is measured. Thus, for example, the depicted profile has a value of about 197 at the 120th slice. (Assuming, for example, that the scanned sheet is 300 inches wide and is divided into 300 equal slices of one-inch width, the 120th slice in the graph of FIG. 1 would be one hundred twenty inches from one edge of the sheet.)

Under ideal conditions, sheet properties are constant from profile to profile and, furthermore, are constant along each profile. Thus, the measured properties shown in the profile of FIG. 1 may be understood to deviate substantially from the ideal in terms of cross-directional uniformity.

Figure 2:
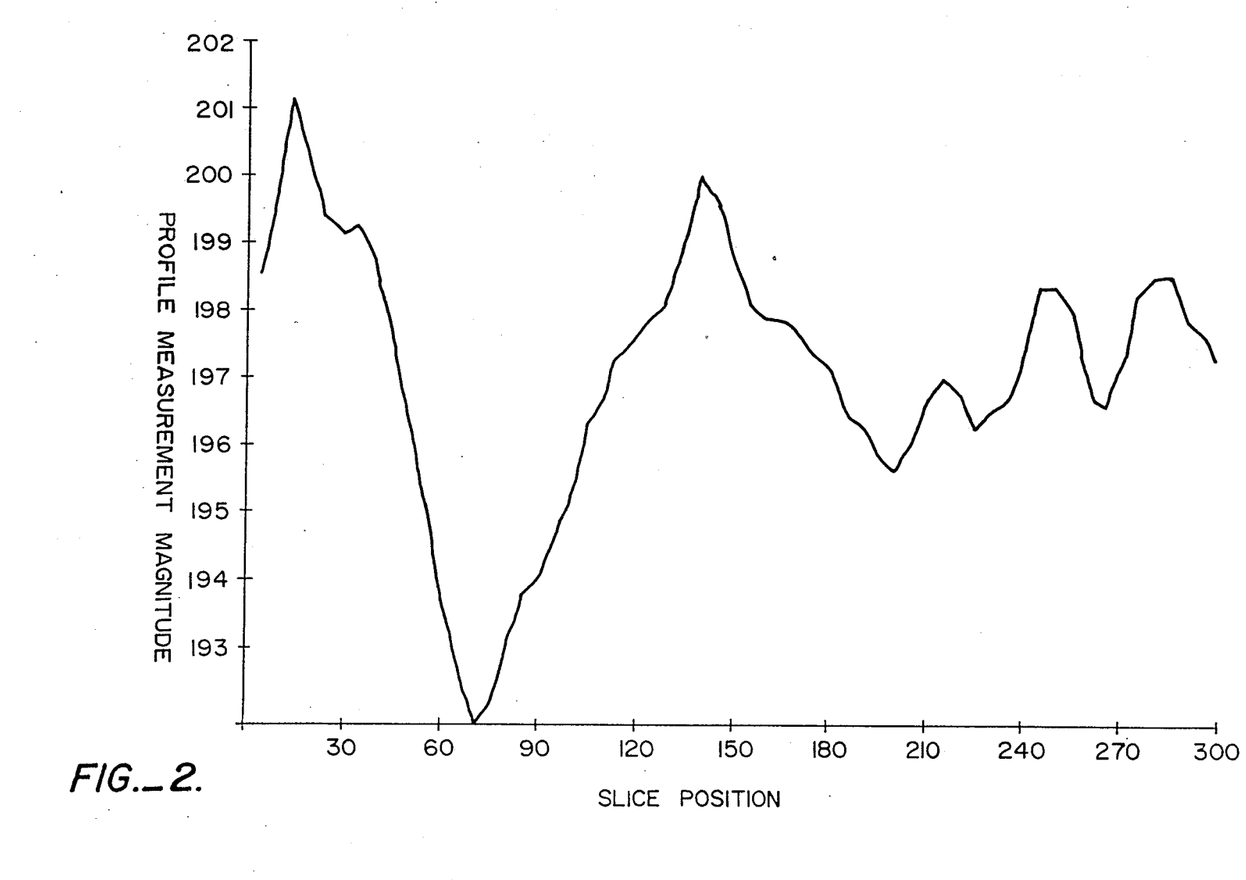
FIG. 2 is a graph depicting only the low spatial-frequency components of the profile of FIG. 1.
Figure 3:
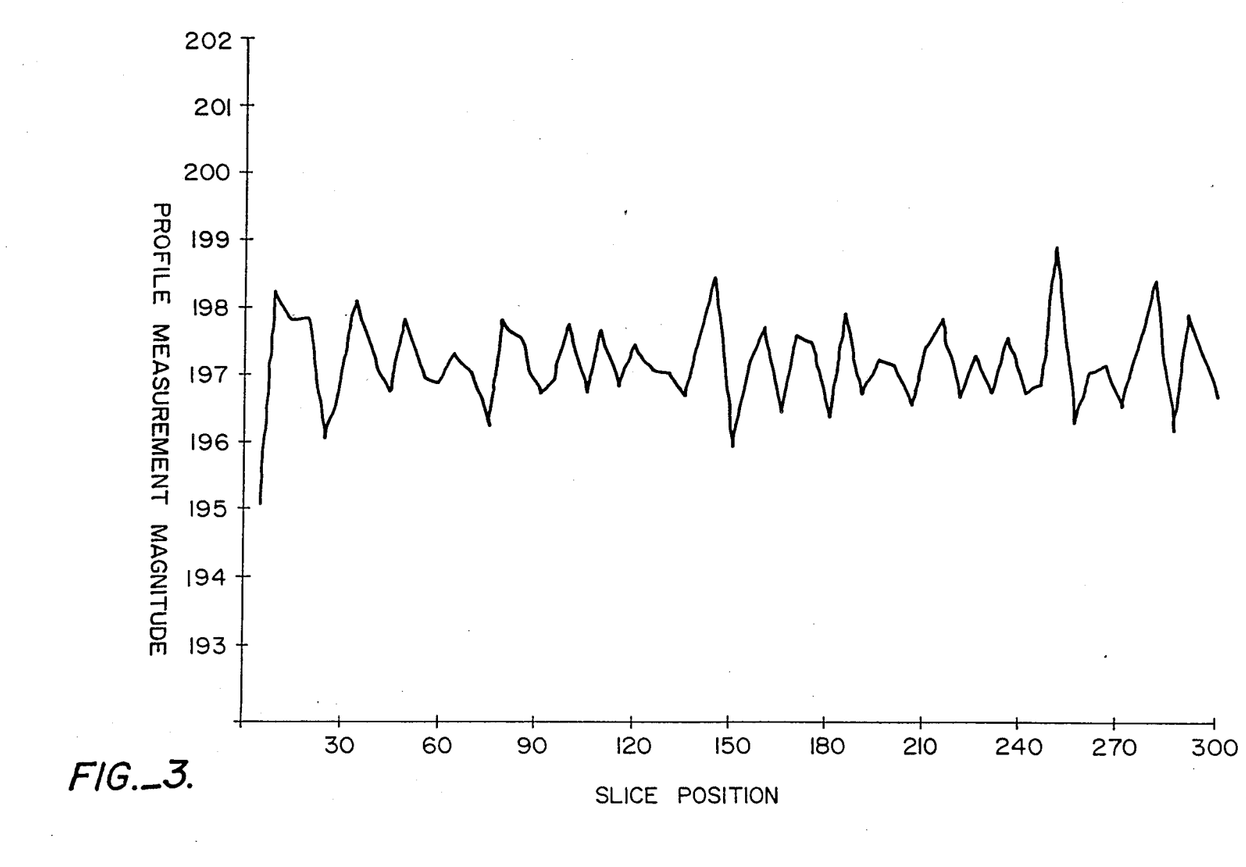
FIG. 3 is a graph depicting only the high spatial-frequency components of the graph of FIG. 1.

By analogy with Fourier spectrum analysis of time-varying signals but measuring frequency in terms of cycles per unit distance in the cross direction instead of cycles per unit time, the profile in FIG. 1 can be said to have low-frequency sinusoidally varying "spatial-frequency" components as well as substantial high-frequency spatial-frequency components, including noise. Following this analogy, FIGS. 2 and 3 show the profile of FIG. 1 separated into low and high spatial-frequency components, respectively. That is, FIG. 2 shows the low spatial-frequency variations in the profile of FIG. 1 and FIG. 3 shows the high spatial-frequency variations. It may be noted that the horizontal and vertical axes have the same scales as in FIG. 1 and that the profile magnitudes in FIGS. 2 and 3 can be summed at each slice location to provide essentially the same profile as in FIG. 1.

In the following, the process of separating high and low frequency components of a cross-directional profile will be referred to as "spatial-frequency splitting". This term is chosen to emphasize the distinction between spatial-frequency signals and time-domain signals. Again, it should be noted that the frequency of time-domain signals is measured in cycles per second, while the frequency of spatial-frequency signals is measured in terms of cycles per unit distance.

Figure 4:
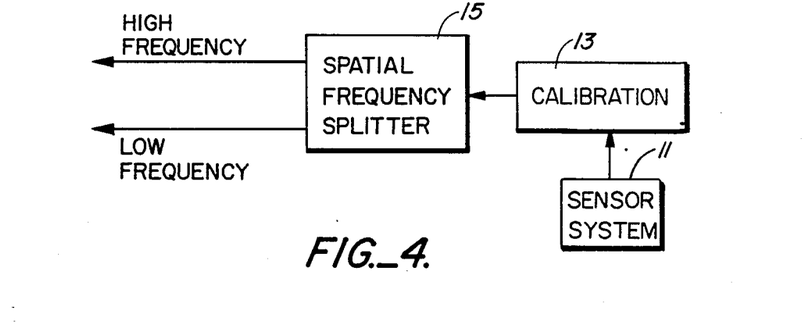
FIG. 4 is a generalized block diagram of a cross-directional control system according to the present invention.

FIG. 4 generally illustrates the components of a system for operating one or more control devices on a sheetprocessing machine based upon a strategy of spatial-frequency splitting. The illustrated system, which generally can be referred to as a multi-frequency actuator control system, includes a sensor system 11, a calibration device 13, and a spatial-frequency splitter 15. The sensor system 11 can be, for example, a conventional scanning sensor which functions to measure a selected property of a sheet at a plurality of consecutive cross-directional locations comprising a "scan". Likewise, calibration device 13 is conventional and serves to calibrate output signals from sensor system 11. If desired, the output signals from calibration device 13 could be assembled over each scan to display cross-directional profiles generally similar to the one shown in FIG. 1.

In operation of the multi-frequency actuator control system of FIG. 4, spatial-frequency splitter 15 functions to decompose calibrated profile measurements into low spatial-frequency and high spatial-frequency components. Normally, the low spatial-frequency components are used to operate a first control device and the high spatial-frequency components are used to operate a second control device, where both control devices affect the same sheet property. For example, the low spatial-frequency components can be used to operate a steambox on a papermaking machine and the high spatial-frequency components can control a remoisturizing shower on the same papermaking machine. As another example, the high spatial-frequency components provided by the multi-frequency actuator control system can control a secondary headbox on a papermaking machine and the low spatial-frequency components can control a primary headbox on the same papermaking machine. As still another example, high spatial-frequency components can be used to control a calendaring system having a plurality of hot air jets for adjusting pressure applied by calendar loading rolls and the low spatial-frequency components can be used to control segments of a sectionalized control crown roll. In the latter example, both the calendaring system and the crown roll are provided to control sheet caliper on the same papermaking machine.

Figure 5:
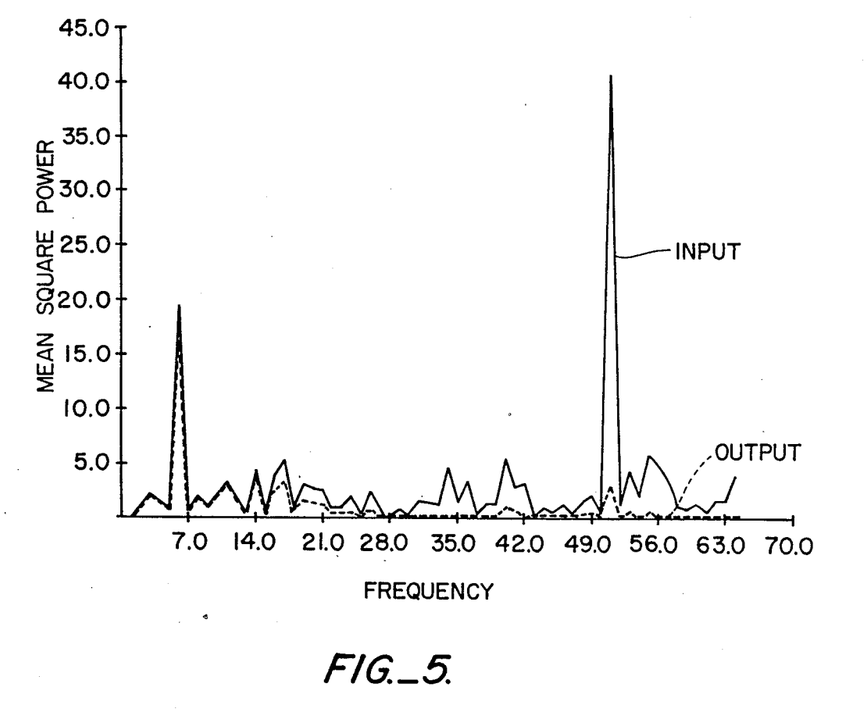
FIG. 5 is a graph depicting frequency spectra of a cross-directional profile operated upon by the system of FIG. 4.

FIG. 5 shows an example of the frequency spectra for a profile received by spatial-frequency splitter 15 and of the low spatial-frequency components provided as the output of the frequency splitter. (It may be noted that the received profile is somewhat different than the profile shown in FIG. 1.) In FIG. 5, values along the vertical axis represent the mean square power of spatial-frequency signals and values along the horizontal axis represent the spatial-frequencies of the signals in cycles per inch. It can be noted that the input spectra is broad, uneven, and displays a relatively high magnitude for spatial frequencies at about seven and at about fifty cycles per inch. By way of contrast, the low-frequency output spectra is relatively smooth at high spatial-frequencies but has a readily distinguished peak at the relatively low frequency of about seven cycles per inch.

At this juncture, it should be appreciated that operation of the spatial-frequency splitter 15 in the multi-frequency actuator control system of FIG. 4 differs substantially from operation of a filter for time-varying signals. In fact, if spatial-frequency components of a cross-directional profile were converted to time-varying signals and then filtered in the same manner that time-varying signals are normally filtered, the filtered profile would be poorly suited for the control of sheet-processing machines. This is because, when time-varying signals are filtered, the output of the filter is normally shifted in time relative to the input, with the extent of the shift depending upon the design of the filter and upon the frequency and amplitude of the time-varying signals received by the filter. By way of contrast, the output of spatial-frequency splitter 15 of FIG. 4 is not shifted or displaced when spatial-frequency components of profile measurements are separated. This can be seen from the graphs of FIGS. 1 through 3, wherein the peaks in the low spatial-frequency and high spatial-frequency components in FIGS. 2 and 3 occur at substantially the same slice locations as the peaks in the composite profile in FIG. 1.

Figure 6:
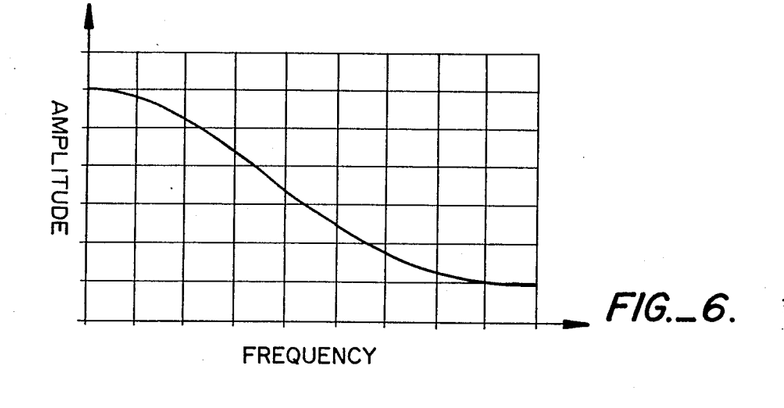
FIG. 6 is an example of a so-called "window function" for use in the system of FIG. 4.

Spatial-frequency splitter 15 of FIG. 4 produces a desired separation of frequencies by smoothing or convolution techniques. Smoothing can be accomplished, for example, by computing the running arithmetical average along a cross-directional profile. In the case of convolution, a cross-directional profile is convolved with a function which produces an output having the desired frequency spectra characteristics. The convolving function can, for the sake of convenience, be referred to as a "window" function. When a cross-directional profile is convolved with a suitable window function, the resulting profile function will display substantially unaltered components of the original profile having spatial-frequencies less than a preselected "cutoff" frequency, but components having spatial-frequencies exceeding the cutoff frequency will be substantially attenuated (i.e., diminished in magnitude). FIG. 6 shows a suitable window function of the type known as a Blackman function; it may be noted that this function has generally constant amplitude over a range of low frequencies and then rapidly decreases to zero at frequencies near the selected cutoff spatial frequency.

The cutoff spatial-frequency also can be defined by a so-called "tuning" factor which, mathematically, is inversely related to the cutoff frequency. Accordingly, for a selected tuning factor, spatial-frequency splitter 15 of FIG. 4 operates to attenuate spatial-frequency components of a cross-directional profile having periods shorter than the tuning factor but generally will not alter spatial-frequency components having periods longer than the tuning factor. Thus, for relatively large tuning factors, the spatial-frequency splitter 15 of FIG. 4 will attenuate all but very low spatial frequencies. In practice, it is convenient to express the tuning factors in terms of actuator zone width.

In practice, tuning factors are selected based upon the characteristics of the control device being operated by the multi-frequency actuator control system. More particularly, tuning factors are usually chosen based upon the cross-directional response characteristics of a given control device. For instance, a primary headbox having an actuator zone width of ten inches might have a response characteristic of about twenty inches per zone, and this would determine the tuning factor chosen to control the headbox (i.e., the tuning factor would be about two slice width per cycle or, equivalently, about twenty inches per cycle). Typically, the tuning factor employed with a given cross-directional control device is no less than twice the actuator zone width of the control device.

Spatial-frequency response characteristics of individual control devices also determine the decision as to which control device, or devices, is to be operated by the low spatial-frequency components and which control device, or devices, is to be operated by the high spatial-frequency components. For instance, a primary headbox having actuator zone widths of ten inches each might be controlled by low spatial-frequency components and a secondary headbox having actuator zone widths of two inches each might be controlled by high spatial-frequency components. It might be noted that, in the papermaking art, control devices that operate near the head of a papermaking machine are usually better suited for control by low spatial-frequency components and, conversely, profiling devices that operate near the reel end of a papermaking machine are usually better suited for control by high spatial-frequency components.

Thus, it can be appreciated that the multi-frequency actuator control system of FIG. 4 provides operating signals which are consistent with the capabilities of the control device receiving the signals. In that sense, the system achieves optimum use of the control device, or devices, which are best suited to adjust process conditions to overcome detected non-uniformities in cross-directional profiles.

Figure 7:
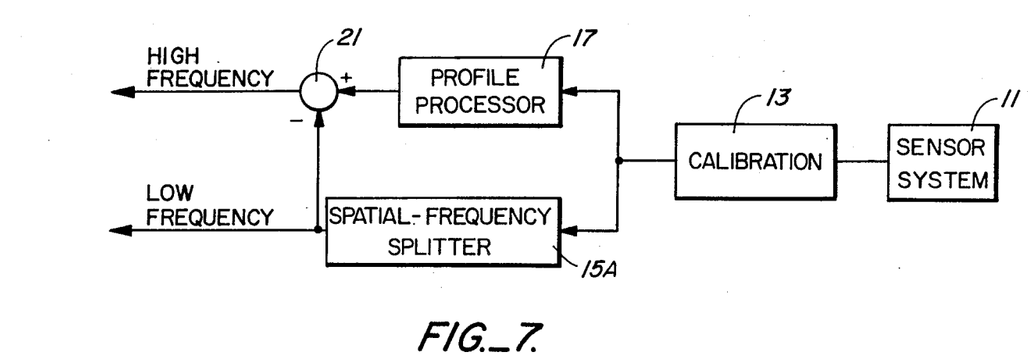
FIG. 7 is a functional diagram of a more detailed embodiment of a system as in FIG. 4.

FIG. 7 illustrates a more detailed embodiment of a multi-frequency actuator control system. In this embodiment, calibration device 13 is connected to both a profile processor 17 and spatial-frequency splitter 15A. Frequency splitter 15A is essentially the same as the device 15 previously described in conjunction with FIG. 4 but, in this illustration, the output comprises only low spatial-frequency components extracted from each calibrated input profile. Profile processor 17 can be understood to be a conventional profile processing device such as the Mini-Slice (TM) processor available from Measurex Corporation of Cupertino, California. For convenience, the output of profile processor 17 will be referred to herein as "processed profiles". The system of FIG. 7 further includes a summer 21 at which the output of frequency splitter 15A is subtracted from the output of profile processor 17. Therefore, the output of summer 21 comprises only high spatial-frequency components of processed profiles.

Operation of the multi-frequency actuator control system of FIG. 7 will now be described. Initially, profile processor 17 computes simple arithmetical averages of the calibrated output signals provided by scanning gauge 11. The averages are normally based upon the widths of actuator zones being controlled by the system. For example, if the actuator control system is to control a remoisturizing shower having forty independent actuator zones of equal width extending across a four-hundred inch sheet, profile processor 17 would normally compute simple arithmetical averages for profile measurements every ten inches. Thus, in this example, the arithmetical average of all of the profile measurements for the first ten inches of a cross-directional scan would be computed by profile processor 17, thereby providing a first value, then the arithmetical average for all of the measurements for the next ten inches of the cross-directional scan would be computed to provide a second value, and so forth, until one hundred average values are computed for the full width of the scanned sheet. In practice, the range over which the averages are computed depends not only on actuator zone width but upon the extent of coupling between actuator zones. Also in practice, it is not necessary that consecutive actuator zones be of equal width. For example, a particular control device for controlling cross-directional sheet properties might have a first actuator zone which is twenty inches wide followed by a number of actuator zones which are each ten inches wide. In that case, profile processor 17 would compute an arithmetical average for the first twenty inches of a cross-directional profile and, thereafter, would compute arithmetical averages in ten inch increments.

Further in operation of the multi-frequency actuator control system of FIG. 7, spatial-frequency splitter 15A is normally operated at a tuning factor greater than unity and, therefore, its output comprises low spatial-frequency components of the calibrated profiles. That is, the output of spatial-frequency splitter 15 normally comprises spatial-frequency components having periods exceeding the tuning factor. The window function employed by spatial-frequency splitter 15A is a matter of design choice.

In comparing the systems of FIGS. 4 and 7, it will be appreciated that spatial-frequency splitter 15 of FIG. 4 combines the functions of profile processor 17 and spatial-frequency splitter 15A of FIG. 7. Thus, to the extent that the capacity to compute arithmetical averages is embodied in a spatial-frequency splitting module, a separate averaging device, or devices, is not required.

At summer 21 in FIG. 7, the output of profile processor 17 is summed with the output of frequency splitter 15A. Thus, for each cross-directional scan, the output of summing node 21 contains only high spatial-frequency components of a processed profile, while the output of frequency splitter 15A contains only low spatial-frequency components of the calibrated profile. Again, the high spatial-frequency components are available to operate a control device, or devices, having relatively high spatial-frequency characteristics, and the low spatial-frequency components are available to operate a different control device, or devices, having low spatial-frequency characteristics.

Figure 8:
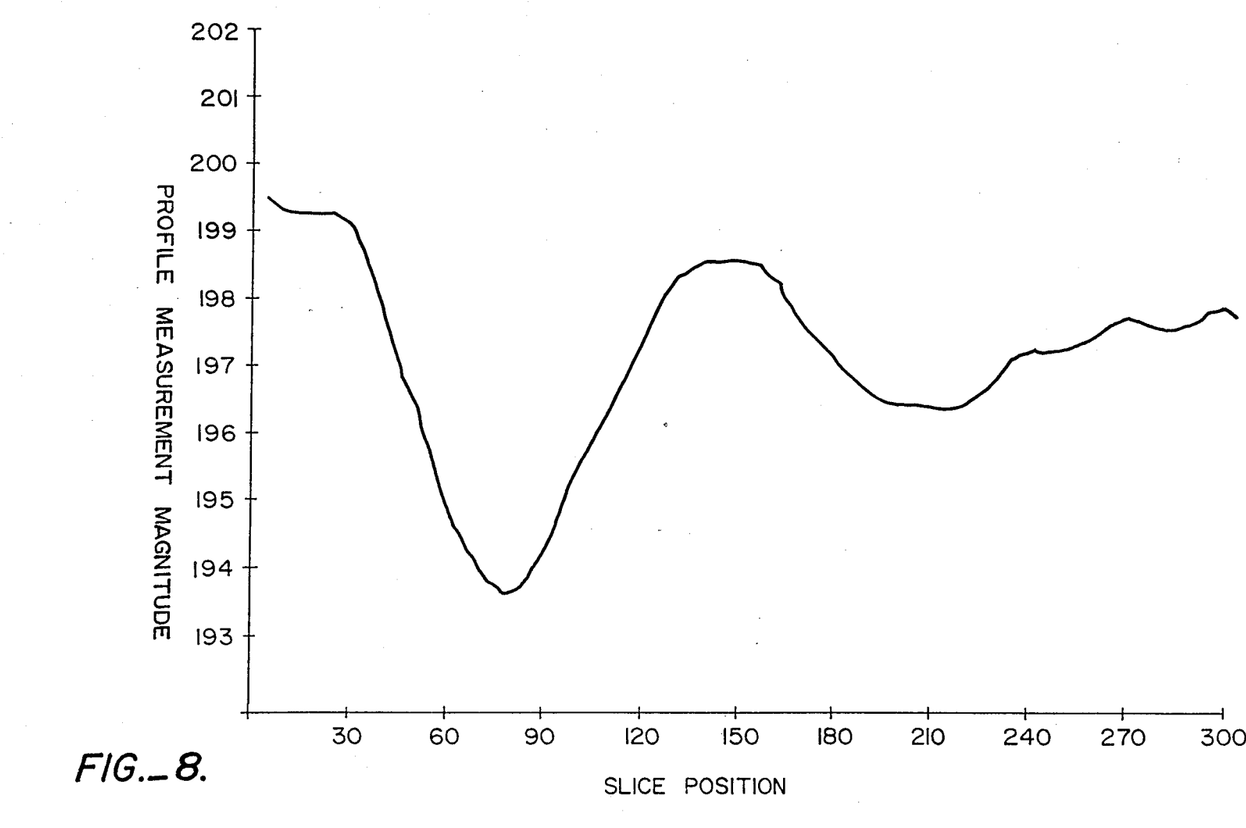
FIG. 8 is a graph depicting an example of another cross-directional profile operated upon by the system of FIG. 4.
Figure 9:
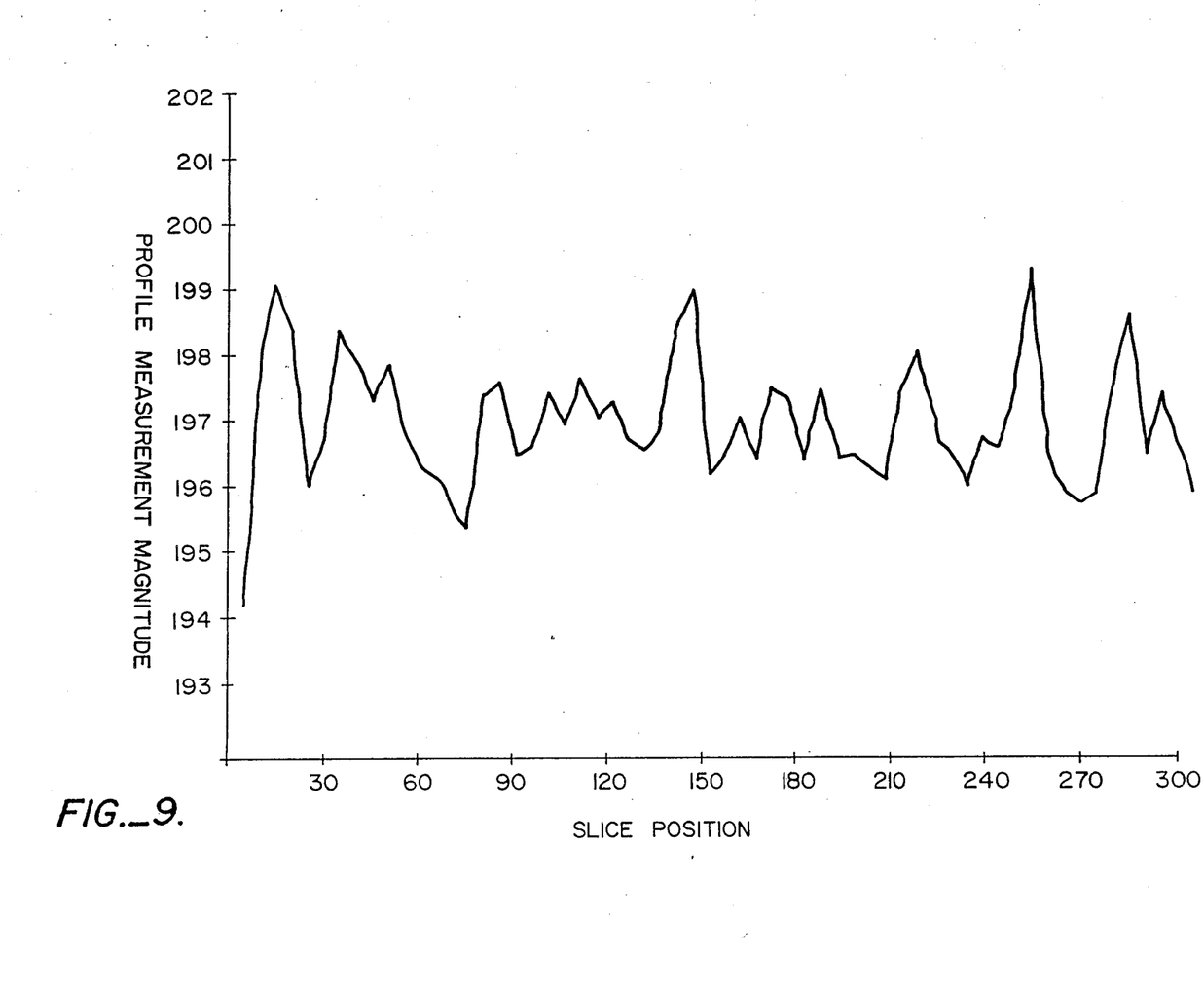
FIG. 9 is yet another example of a cross-directional profile operated upon by the system of FIG. 4.

FIGS. 8 and 9 illustrate the effect of different tuning factors on output control signals provided by the systems of FIGS. 1, 4 and 7. Specifically, FIGS. 8 and 9 show low and high spatial-frequency profiles, respectively, derived from the profile of FIG. 1 using a tuning factor of eight. These profiles can be contrasted with the profiles shown in FIGS. 2 and 3, which were obtained with a tuning factor of three. Thus, the low spatial-frequency profile of FIG. 2 was obtained by employing a higher cutoff frequency than the profile of FIG. 8 and, therefore, the former profile is somewhat more irregular since it contains relatively fewer low spatial-frequency components. Conversely, the high spatial-frequency profile of FIG. 3 is less irregular than the profile of FIG. 9 since the former profile contains relatively more low spatial-frequency components.

Figure 10:
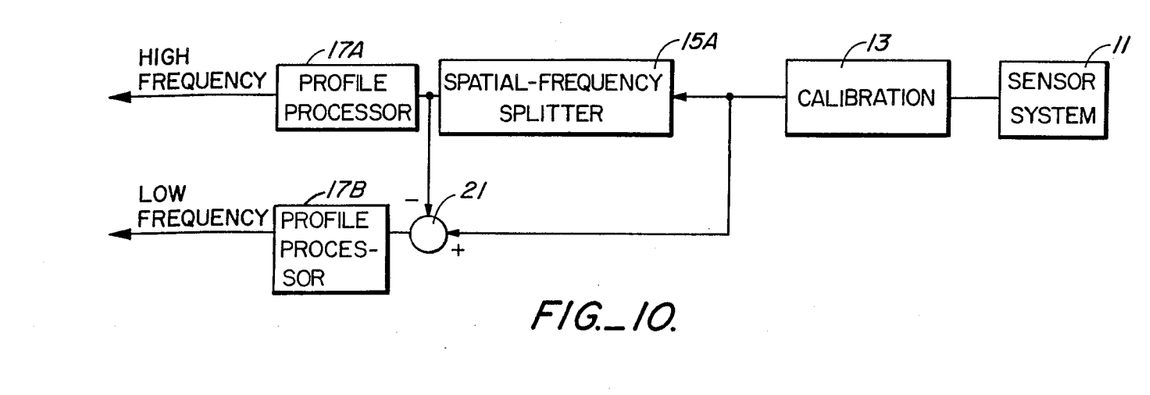
FIG. 10 is a block diagram of an alternative embodiment of a cross-directional control system according to the present invention.

FIG. 10 shows an alternative embodiment of a multi-frequency actuator control system. In this embodiment, calibration device 13 is connected to provide input to both frequency splitter 15A and summer 21. The low spatial-frequency output of frequency splitter 15A is provided to both the inverting (negative) input of summer 21 and to a first profile processor 17A. Further, the output of summer 21 is provided to a second profile processor 17B. Both profile processors 17A and 17B can be understood to operate in substantially the same manner as the above-described profile processor 17.

In operation of the multi-frequency actuator control system of FIG. 10, frequency splitter 15A produces an output comprising low spatial-frequency components of the calibrated profiles. (Again, the exact output of frequency splitter 15A depends upon the selected tuning factor and the selected window function.) At summer 21, the low frequency components are subtracted from the calibrated profiles, so that the output of the summer comprises the high frequency components of the calibrated profiles. Then, the low spatial-frequency components are averaged by first profile processor 17A and the high spatial-frequency components are averaged by second profile processor 17B. The averaged low spatial-frequency components are available to operate control devices having low frequency response characteristics and the high spatial-frequency components are available to operate control devices having high frequency response characteristics. It may be noted that the two profile processors 17A and 17B are employed when different control devices have different numbers of actuator zones. In practice, control devices which are best suited for operation by high spatial-frequency components often have a greater number of actuator zones than control devices suited for control by low spatial-frequency components.

Figure 11:
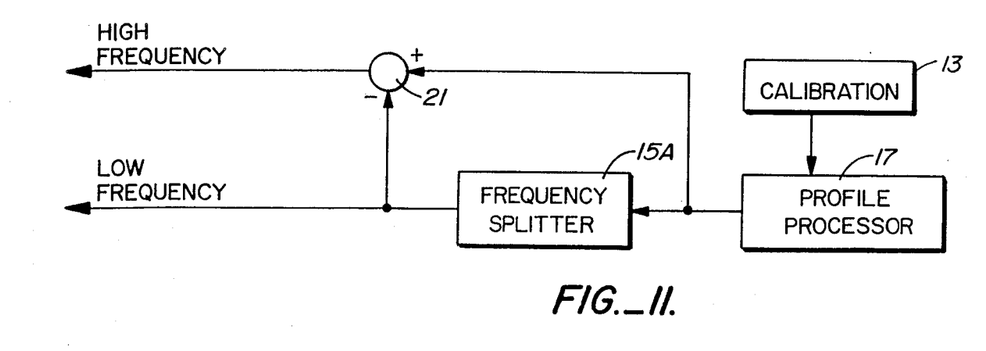
FIG. 11 is a block diagram of yet another alternative embodiment of a cross-directional control system according to the present invention.

FIG. 11 shows yet another alternative embodiment of a multi-frequency actuator control system. In this embodiment, calibration device 13 is connected to provide input to profile processor 17. The output of profile processor 17 is provided to both a summer 21 and a frequency splitter 15A. Further, the low spatial-frequency output of frequency splitter 15A is provided to summer 21 for subtraction from the output of profile processor 17.

In operation of the multi-frequency actuator control system of FIG. 11, calibrated profiles are averaged by profile processor 17 and provided to frequency splitter 15A to produce an output comprising low spatial-frequency components of the averaged profiles. Again, the exact nature of the spatial frequency components in the output of the frequency splitter depend upon the selected tuning factor and the selected window function. Then, at summer 21, the low spatial-frequency components are subtracted from the averaged profiles so that the output of the summer comprises the high frequency components of the averaged profiles. Thus, the system of FIG. 11, like the above-described alternative embodiments, provides low spatial-frequency signals for use in controlling cross-directional profiling devices having low spatial-frequency response characteristics and, separately, provides high spatial-frequency signals for use in controlling cross-directional profiling devices having high spatial-frequency response characteristics.

Although preferred embodiments of multi-frequency actuator control systems according to the present invention have been described, those skilled in the art will appreciate that additions, modifications, substitutions and deletions not specifically described in the foregoing may be made without departing from the spirit and scope of the present invention. For example, the above-described systems can be modified to divide profiles into three ranges of spatial frequencies so that different control devices can be operated according to each of the three ranges of frequencies. Also, measurements from two or more measurement devices can be combined to provide composite measurement profiles and, then, those composite profiles can then be decomposed into selected spatial-frequency components to provide separate control signals.

Still further, although the present invention has been described in terms of control of cross-directional properties, and it may be that the benefits of the present invention are best realized in that embodiment, the basic techniques underlying the invention can be applied to control of machine-direction properties. Thus, for selected slices, variations between consecutive profiles can be computed and then the variations can be analyzed in terms of their spatial-frequency components. In turn, low and high spatial-frequency components of the machine direction variations can be employed to separately operate different control devices so that, for a given irregularity in machine-direction properties, correction of the irregularity can be accomplished by the control device best capable of achieving the correction.

I claim:

1. A system for controlling cross-directional sheet properties during production of sheets on sheet processing machines, comprising:
    measurement means for providing measurements of at least one property of a sheet during production, which measurements are made at a plurality of cross-directional locations that successively span the sheet;
    means for assembling the measurements to provide cross-directional profiles of the sheet;
    spatial-frequency splitting means for operating upon the cross-directional profile measurements to separate selected spatial-frequency components from each cross-directional profile to provide operating signals to cross-directional control devices based upon the separated spatial-frequencies.

2. A system according to claim 1 wherein the spatial-frequency splitting means separates high spatial-frequencies from low spatial-frequencies for each cross-directional profile.

3. A system according to claim 1 wherein the spatial-frequency splitting means separates high spatial-frequencies from low spatial-frequencies by computing a running average of measurements for each profile.

4. A system according to claim 1 wherein the spatial-frequency splitting means identifies low spatial-frequencies for each cross-directional profile, computes a low spatial-frequency profile for each cross-directional profile, and then subtracts the computed low spatial-frequency profile from the cross-directional profile from which it was derived to provide a high spatial frequency profile.

5. A system according to claim 1 wherein the spatial-frequency splitting means separates high spatial-frequencies from low spatial-frequencies by convolution.

6. A system according to claim 5 wherein the convolution is accomplished by convolving cross-directional profiles with a Blackman-type function.

7. A system according to claim 1 further including averaging means operative upon the selected spatial-frequency components to compute arithmetical averages for selected groups of the components.

8. A system for controlling cross-directional sheet properties on sheet processing machines, comprising:
    measurement means for providing measurements of a property of a sheet during production, which measurements are made at a plurality of cross-directional locations that successively span the sheet and which can be assembled to provide cross-directional profiles of the sheet;
    averaging means for computing arithmetical averages of selected groups of the cross-directional measurements provided by the measurement means;
    spatial-frequency splitting means for operating upon the averaged cross-directional values provided by the averaging means to separate selected spatial-frequency components from the profile of measurements for each cross-directional profile, which separated spatial-frequency components can be employed for operating devices to control sheet properties in the cross direction.

9. A system according to claim 8 wherein the spatial-frequency splitting means separates high spatial-frequencies from low spatial-frequencies for each cross-directional profile.

10. A system according to claim 8 wherein the spatial-frequency splitting means separates high spatial-frequencies from low spatial-frequencies by computing a running average of measurements for each profile.

11. A system according to claim 8 wherein the spatial-frequency splitting means separates high spatial-frequencies from low spatial-frequencies by convolution.

12. A system according to claim 8 wherein the spatial-frequency splitting means identifies low spatial-frequencies for each cross-directional profile, computes a low spatial-frequency profile for each cross-directional profile, and then subtracts the computed low spatial-frequency profile from the cross-directional profile from which it was derived to provide a high spatial frequency profile.

13. A system for operating cross-directional control devices on sheet producing machines, comprising:
    measuring means for providing measurements of at least one property of a sheet at cross-directional locations, which measurements can be assembled to provide cross-directional profiles of the at least one property;
    spatial-frequency splitting means for separating, for each cross-directional profile, low spatial-frequency components from high-spatial frequency components to provide operating signals to devices that controllably adjust properties of a sheet at cross-directional locations.

14. A system according to claim 13 wherein the spatial-frequency splitting means separates high spatial-frequencies from low spatial-frequencies by computing a running average of measurements for each profile.

15. A system according to claim 13 wherein the spatial-frequency splitting means identifies low spatial-frequencies for each cross-directional profile, computes a low spatial-frequency profile for each cross-directional profile, and then subtracts the computed low spatial-frequency profile from the cross-directional profile from which is was derived to provide a high spatial frequency profile.

16. A process for providing cross-directional control in sheet production system, comprising the steps of:
    measuring a traveling sheet at a plurality of cross-directional locations to provide profiles, based upon the cross-directional measurements, of at least one selected property of the sheet;
    for the plurality of measurements in each cross-directional profile, separating selected spatial-frequency components of the cross-direction profile from other spatial-frequency components; and
    controlling the sheet production system based upon the separated spatial-frequency components of the cross-directional profiles.

17. A process according to claim 16 wherein the step of separating selected spatial-frequency components comprises separating high spatial-frequencies from low spatial-frequencies for each cross-directional profile.

18. A process according to claim 17 wherein the step of separating high spatial-frequencies from low spatial-frequencies comprises computing a running average of measurements for each scan.

19. A process according to claim 17 wherein the step of separating low spatial-frequencies is accomplished by computing a low spatial-frequency profile for each cross-directional profile and then subtracting the computed low spatial-frequency profile from the profile from which it was derived to provide a high spatial frequency profile.

20. A process according to claim 17 wherein the high spatial-frequencies are separated from low spatial-frequencies by convolution.

21. A process according to claim 17 wherein the convolution is accomplished by convolving cross-directional profiles with a Blackman-type function.

22. A process according to claim 17 further including computing arithmetical averages for selected groups of the separated components.

23. A system for controlling sheet properties during production of sheets on sheetprocessing machines, comprising:

measurement means for providing measurements of at least one property of a sheet during production, which measurements are made at a plurality of machine-directional locations along the same slice location on a sheet;

spatial-frequency splitting means for operating upon the output of the measurement means to separate selected spatial-frequency components to provide operating signals to control devices based upon selected spatial-frequencies to control the measured property of the sheet in the machine direction.

24. A system according to claim 23 wherein the spatial-frequency splitting means separates high spatial-frequencies from low spatial-frequencies by convolution.

* * * * *